(12) United States Patent
Ferreira Da Silva

(10) Patent No.: US 11,815,502 B2
(45) Date of Patent: Nov. 14, 2023

(54) LASER-ENERGIZED HEATING SYSTEM IN CARBONATE ROCK ACIDIFICATION TESTS

(71) Applicant: Petróleo Brasileiro S.A.—Petrobras, Rio de Janeiro (BR)

(72) Inventor: Mario Germino Ferreira Da Silva, Rio de Janeiro (BR)

(73) Assignee: Petróleo Brasileiro S.A.—Petrobras, Rio de Janeiro (BR)

( * ) Notice: Subject to any disclaimer, the term of this patent is extended or adjusted under 35 U.S.C. 154(b) by 194 days.

(21) Appl. No.: 17/514,946

(22) Filed: Oct. 29, 2021

(65) Prior Publication Data
US 2022/0146486 A1    May 12, 2022

(30) Foreign Application Priority Data
Nov. 6, 2020  (BR) .................. 10 2020 022705 0

(51) Int. Cl.
*G01N 33/24* (2006.01)
*G01N 15/08* (2006.01)
*G01N 1/44* (2006.01)

(52) U.S. Cl.
CPC .............. *G01N 33/24* (2013.01); *G01N 1/44* (2013.01); *G01N 15/0806* (2013.01)

(58) Field of Classification Search
CPC .......... G01N 33/24; G01N 1/44; G01N 21/01; G01N 15/0826; G01N 15/088; E21B 43/25
See application file for complete search history.

(56) References Cited

U.S. PATENT DOCUMENTS

| 8,627,901 B1* | 1/2014 | Underwood .............. E21B 7/14 175/11 |
| 9,669,492 B2* | 6/2017 | Linyaev ................. B23K 26/38 |
| 9,719,302 B2* | 8/2017 | Linyaev ................. E21B 43/26 |

FOREIGN PATENT DOCUMENTS

| CN | 110441213 B | * | 9/2020 |
| CN | 111610136 A | * | 9/2020 |
| CN | 112798491 A | * | 5/2021 |
| CN | 113008750   | * | 6/2021 |
| CN | 113504168 A | * | 10/2021 |
| CN | 115046897 A | * | 9/2022 |

OTHER PUBLICATIONS

Silva et al. (2013) "Use of Lasers for Perforating Oil Wells", Pontifical Catholic University of Rio de Janeiro, 180 pages.

* cited by examiner

*Primary Examiner* — Francis C Gray
(74) *Attorney, Agent, or Firm* — Mintz Levin Cohn Ferris Glovsky and Popeo, P.C.

(57) ABSTRACT

This invention is in relation to a laser-energization system to be used in laboratory tests used in the area of acid stimulation of carbonate reservoirs aiming to improve the efficiency in the passage of acid inside the reservoir rock. This system improves planning of the operation, seeking more efficient penetration of the acid treatment in the carbonate rock, and therefore it contributes to improving the IP result of the well by increasing the area open to the flow between the reservoir and the well. The laser-energization system comprises coupling the plug-flow testing equipment with the laser-energization system.

4 Claims, 3 Drawing Sheets

LASER-ENERGIZED HEATING SYSTEM IN CARBONATE ROCK ACIDIFICATION TESTS

CROSS-REFERENCE TO RELATED APPLICATIONS

This application claims priority to Brazilian Application No. 10 2020 022705 0, filed on Nov. 6, 2020, and entitled "LASER-ENERGIZED HEATING SYSTEM IN CARBONATE ROCK ACIDIFICATION TESTS," the disclosure of which is incorporated herein by reference in its entirety.

FIELD OF THE INVENTION

The present invention is in relation to a laser-energization system to be used in laboratory tests applied in the area of acid stimulation of carbonate reservoirs that seeks to improve efficiency in the passage of acid inside the reservoir rock. This system improves operation planning, as it seeks greater efficiency in the penetration of acid treatment into carbonate rock, and therefore contributes to improving the well's IP result by increasing the area open to the flow between the reservoir and the well.

DESCRIPTION OF THE STATE OF THE ART

The formation of carbonate rocks is quite varied, which is a function of the processes by which they formed in nature over geological eras, as described in the studies by KARMANN, I.; SANCHEZ, LE "Distribuição das Rochas Carbonáticas e Provincias Espeleológicas do Brasil" [Distribution of Carbonate Rocks and Speleological Provinces of Brazil], Espeleo-Tema, Informative Bulletin No. 13, 1979; TONIETTO, SN "Diagênese e hidrotermalismo em rochas carbonáticas proterozóicas: Grupos Bambuí e Vazante, Bacia do São Francisco" [Diagenesis and hydrothermalism in Proterozoic carbonate rocks: Bambuí and Vazante Groups, São Francisco Basin], 167p. Dissertation (Masters in Geology), University of Brasilia—UnB, 2010; FARIA, R. T. "Tratamento de dados multivariados através da análise de correspondência em rochas carbonáticas" [Treatment of multivariate data through correspondence analysis in carbonate rocks], 151p. Dissertation (Masters) in Geosciences, State University of Campinas, S P, 1993; BARBOSA, J A et al. "Paleoambientes e icnofácies da sequência carbonática da bacia da Paraiba (cretáceo-paleogeno), nordeste do Brasil [Paleoenvironments and ichnofacies of the carbonate sequence of the Paraiba basin (Cretaceous-Paleogene), northeastern Brazil], Revista Brasileira de Geosciences [Brazilian Geosciences Magazine], vol. 36, pp. 449-464, 2006.

The issue is that these rocks may be subject to extremely varied types of impacts, such as acid rain, depositional system, formation of the types of shells that gave rise to carbonate rock, and tectonic movements, among others. In general, the literature is rich in a wide variety of studies on this subject, and the studies are often geared toward the environment of carbonate rock formation in nature. Therefore, the characteristics of this rock, such as permeability, porosity, chemical composition, the presence of empty spaces, natural cracks, etc., may vary depending on the process that gave rise to the formation of the rock in nature.

In the acidification of carbonates, it is well known that there are chemical reactions whose results can be measured to verify the gain in permeability, porosity, and even connectivity of the reservoir to the oil well, whose final objective will be to increase the productivity of the wells in an oil field. However, the kinetics of these reactions are influenced by temperature, that is, the reaction speed increases with higher temperatures.

In offshore acidification operations in water depths above 700 meters, the temperature of the seabed is 4° C. with line lengths depending on the project, and the oil well may be as far as 10 km away from the Stationary Production Unit (SPU), which causes the acid to cool. The speed of the acid reaction will therefore be lower due to the low temperature. For example, with hydrochloric acid and with acetic acid, respectively, the reactions may be summarized as follows:

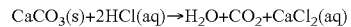

$CaCO_3(s)+2HCl(aq)\rightarrow H_2O+CO_2+CaCl_2(aq)$

$CaCO_3+2CH_3COOH\leftrightarrow Ca(CH_3COO)_2+CO_2+H_2O$

It should also be emphasized that the choice of production strategy is one of the most important tasks in ensuring the success of oil field development. This is because during their useful life oil fields go through different phases, ranging from the beginning of field production to their mature phase. Workover operations are performed in order to maintain the productivity of the wells and thus the useful life of the oil field.

During the productive life of the field several changes occur in the composition of the oil produced, the content of dissolved gas in the oil (RGO), the concentration of water in the oil (BS&W), the composition of the salts present in this water, and the moment gas injection begins via gas lift for artificial oil lifting, among other matters. These changes generate the need to make adjustments in the production conditions of the wells, which changes are adjusted during the useful life of the well with the objective of producing the maximum amount of oil as economically as possible.

Some steps are necessary in the completion phase of the well in carbonate formations, the first being the perforating operation to connect the reservoir to the well. This operation creates a kind of tunnel that will allow oil to flow from the reservoir to the inside of the well. The perforation operation is carried out using cannons lowered by cables, which have explosives designed for this purpose. Next an acidification operation is performed, which seeks to remove the damage caused on the internal faces of the well by the drill bit on the surface of the carbonate rock during the well-drilling process. Such damage causes a reduction in well productivity, and an acid injection treatment is usually performed to improve the assumed drop in productivity.

Treatment with acid injection is subject to scenario variations, such as: differences in the permeability of the formation, in which acid enters more easily where it is more permeable, and where there are fractures. Finally, a last question is about the effect of the treatment, usually on the surface of the rock or the tunnel that was created by the cannon, and sometimes it is even necessary to use chemical divergent to direct the acid treatment to formations with low permeability.

Acidification operations in carbonate formations have shown that the injection of an acid treatment usually depends on the preferential path that is available inside the well at the interface with the reservoir and/or the perforations, in the regions of greater permeability, and/or the presence of natural fractures that can form preferential paths in the rock surface. However, there is a tendency for the treatment to dissolve more on the rock face than to penetrate into the formation, that is, the acid is consumed at the reservoir-well interface.

The study by SILVA, M D; SOARES, J A; LIMA, A. "Efeito da acidificação de matriz sobre a petrofisica de rochas carbonáticas," [Effect of matrix acidification on the petrophysics of carbonate rocks], VII Brazilian Geophysical Symposium, Ouro Preto, Oct. 25-27, 2016, is in relation to natural and artificial carbonate samples that were analyzed for their petrophysical properties before and after a matrix acidification process. Therefore, it is simply laboratory research that monitors petrophysical changes in a representative rock sample, without the use of a laser-energization tool.

Document PI10058680A2 reveals a thermochemical process for acidification of oil or gas wells, water or gas injectors, and removal of mortar in long horizontal wells, or even acidifications that seek to restore the permeability of these wells. This process is applied directly to the oil well and makes no mention of equipment associated with a method of using a laser for photonic and thermal catalysis for the acid reaction.

The reference by SILVA, MGF "Aplicação de laser para canhoneio de poços de petróleo," [Use of lasers for perforating oil wells], 180p., Dissertation (Masters in Mechanical Engineering), Pontifical Catholic University of Rio de Janeiro, 2013, reveals a study aimed at evaluating the use of high-power lasers for perforating operations in coated and cemented wells in carbonate reservoirs, whose objective is to introduce lateral holes directly into the well walls to allow the flow of fluid from the reservoir to the well.

Thus, no prior document in the state of the art reveals a laser-energization system in plug tests to evaluate carbonate acidification such as the system in this invention.

This invention was developed to solve these types of problems, which, through the results of a study to evaluate the behavior of the passage of acid through a plug-shaped sample from the reservoir rock that will be acidified, aims to improve the planning of the operation and thus seek greater efficiency in the penetration of acid treatment into the carbonate rock, and therefore contribute to improving the well's IP result, by increasing the area open to the flow between the reservoir and the well.

That said, the present invention presents a technological solution for planning the production development in oil fields, such as the pre-salt, in order to increase the recovery factor of oil fields in order to thus obtain a better result that is more economical.

It should also be noted that the present invention is in relation to a specific phase of the field's productive life, the start of production, but it may also be applied in workover operations when the gas lift and low BS&W scenario occur in field production management, and thus necessarily the entire productive life of the field; therefore it is a solution wherein there is better reservoir and field production management in order to be as economic as possible.

BRIEF DESCRIPTION OF THE INVENTION

This invention is in relation to a laser-energized system to improve the productivity of drilled and completed wells in carbonate formations. Therefore, this technology to study and predict, through laboratory tests, improves planning of the operation and thus seeks greater efficiency in the penetration of acid treatment in carbonate rock and consequently contributes to improve the IP result of the well, by increasing the area open to the flow between the reservoir and the well.

This invention is used in the area of acid stimulation in carbonate reservoirs, such as the pre-salt.

BRIEF DESCRIPTION OF THE DRAWINGS

This invention will be described in more detail below, with reference to the attached figures which, in a schematic and non-limiting way, show examples of its embodiment. The drawings are as follows.

DETAILED DESCRIPTION OF THE INVENTION

Figure 1:
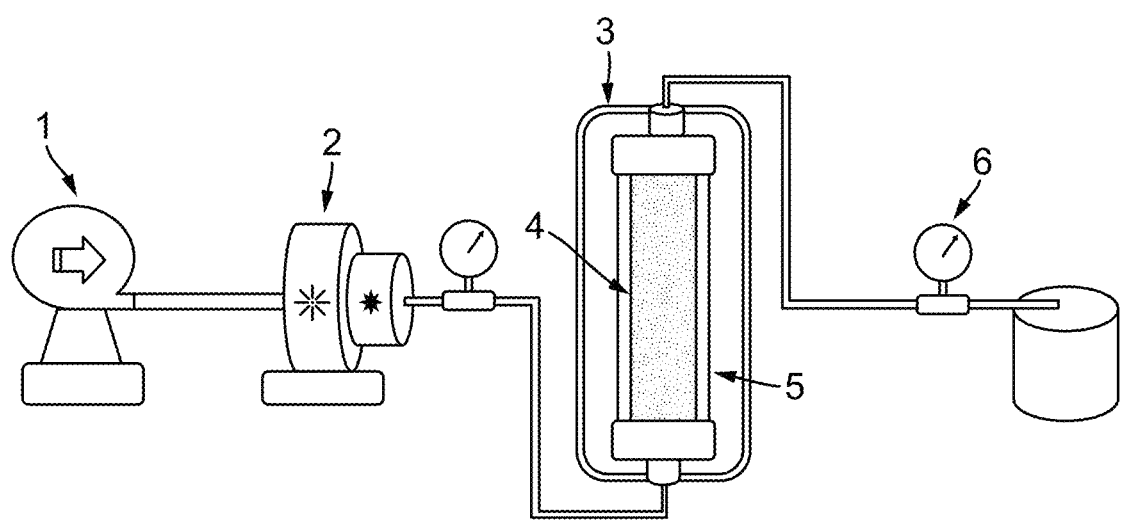
FIG. 1 illustrating a design of the laser-energized and heating system in plug tests for carbonate acidification evaluation according to this invention, showing a: (1) pump, (2) laser-energization system, (3) plug-flow testing equipment, (4) rock plug, (5) holder and (6) manometer.

The laser-energization system used in plug testing in laboratory tests according to the present invention and illustrated in FIG. 1 comprises a pump for fluid displacement (1), plug testing equipment (3) coupled to the laser-energization system, (2) and a manometer (6) so that laser energization in the acid during the test will increase the diameter of the channels created during acidification, thus increasing the reactivity of the acid due to the presence of photons and to the increase in temperature, also promoting the result in the reaction kinetics between the acid and the rock plug, that is, consumption of the rock mass by the acid will be greater.

Figure 2:
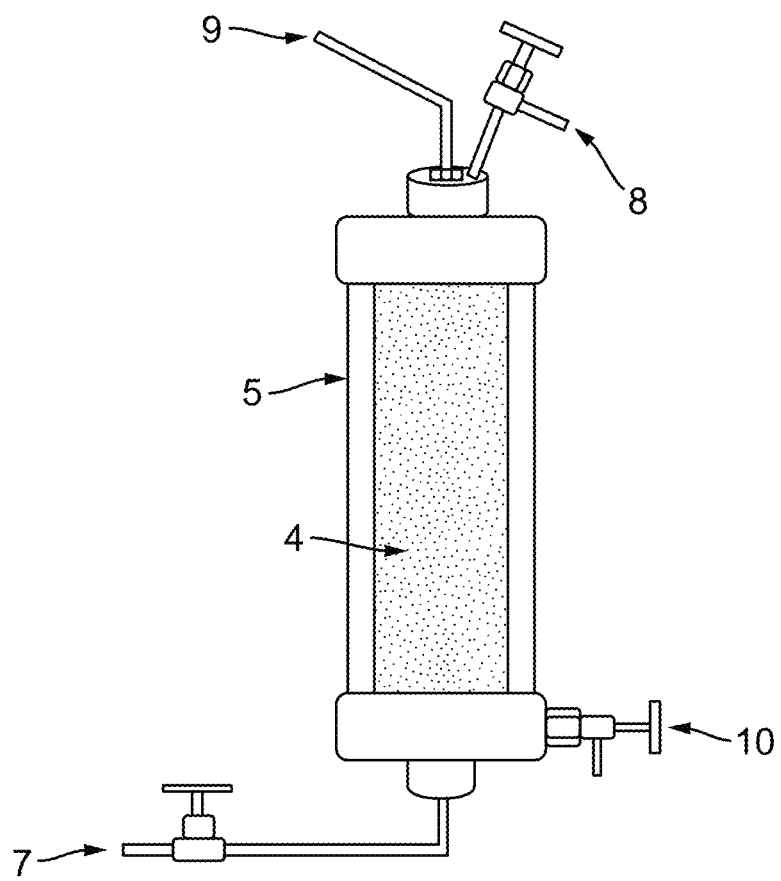
FIG. 2 illustrating rock-plug testing equipment that has a fluid inlet centered on the lower part of the body of the holder, a lateral drainage system at the base of the body of the holder, a pressurization system, and a fluid outlet centered on the upper part of the holder.
Figure 3A:
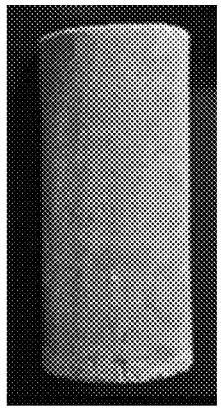
FIG. 3 illustrating the plugs from samples A to F of carbonate reservoir rock from different fields, which will be subjected to structural verification tests of the plugs through micro tomography, before laser-energized acidification, and after acidification for evaluation of the channel created on each plug sample.
Figure 3B:
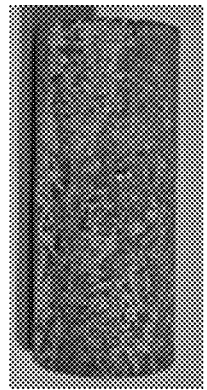
Figure 3C:
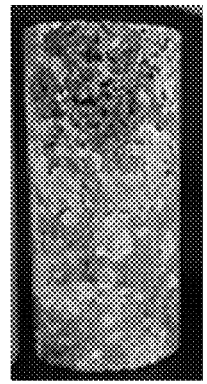
Figure 3D:
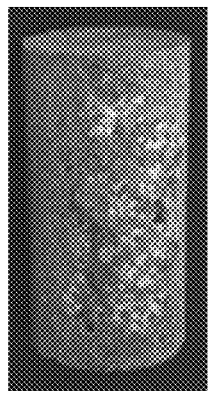
Figure 3E:
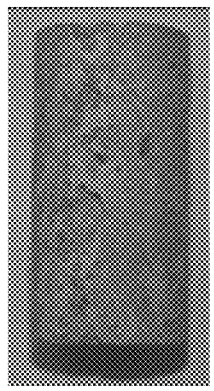
Figure 3F:
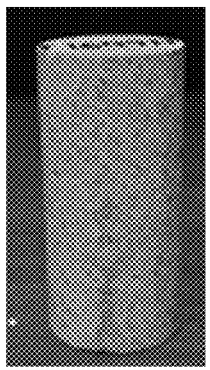

As shown in greater detail in FIG. 2, the plug-testing equipment (3), contains an acid inlet (7) on the lower portion of the holder (5), and an acid outlet (8) on the upper portion, a nitrogen line (9) for pressurizing the holder to simulate reservoir pressure, and a valve line (10) for purging the nitrogen and liquid left inside the holder after the test is finished.

Before designing an acidification program for a carbonate rock, a laboratory study is performed to evaluate the behavior of the passage of the acid through a plug-shaped sample from the reservoir rock that will be acidified. The objective of this test is to verify how the plug will behave with the passage of acid, which may be formic, acetic, hydrochloric and/or gelled acid.

From the result of this laboratory test, the analyst will verify and infer how the acid will be distributed within the reservoir rock. The result of the test improves operation planning, and thus greater efficiency in the penetration of acid treatment into carbonate rock, and it therefore contributes to improving the well's IP result by increasing the area open to the flow between the reservoir and the well.

This invention proposes to include the use of acid energization in laboratory tests by using laser radiation to increase the acid reactivity in order to increase the efficiency of these carbonate rock acidification tests.

The reaction of HCl acid 15% with the carbonate rock consisting basically of $CaCO_3$ produces $CO_2$, $CaO$ and $H_2O$. When applied to carbonate rocks, laser radiation causes thermal degradation of around 800° C., $CaCO_3$ produces $CaO$ and $CO_2$. Temperature is one of the factors that most heavily impacts the speed of a reaction. An increase in temperature therefore not only increases the frequency of collisions between reacting molecules, but also the energy with which the molecules collide.

According to collision theory, the probability of the molecules reacting increases, that is, the speed of the reaction increases. From inorganic chemistry, the increase in temperature within a certain range changes the reaction kinetics, increasing its speed. Once the ideal parameters are adjusted, which parameters do not rely solely on temperature, they may be dependent on the chemical components of the carbonate rock sample in the scenario where the technological solution will be applied.

The association of the acid and the laser in the laboratory testing equipment therefore produces more efficient results in terms of the chemical reaction between the HCl acid 15% and the $CaCO_3$ present in the formation sample plug.

In laboratory tests, the studies performed using the proposed laser-energization system showed the level of real gain obtained by using laser-energized acid in relation to the plug. It is sufficient to perform petrophysical tests to measure the permeability and porosity of the rock before and after testing in order to measure what the gain will be by using the laser-energization technique on the acid.

This invention is therefore a way to evaluate the productivity gain in the wells of an oil field in a carbonate formation where laser-energized acidification technology is applied, and it then becomes possible to plan the field's increased recovery factor through its increased productivity.

It should be noted that although the present invention has been described with respect to the attached drawings, it may undergo modifications and adaptations by those skilled in the art, depending on the specific situation, but provided that it is within the inventive scope defined herein.

The invention claimed is:

1. A laser-energized heating system for carbonate rock acidification testing, the system comprising:
    a pump for fluid displacement; and
    equipment for plug-flow testing coupled to a laser-energized system and a manometer, wherein the equipment comprises a holder with an acid inlet on a lower portion of the holder and an acid outlet on an upper portion of the holder, and a gas pressurization line.

2. The system of claim 1, wherein the laser-energized system is positioned before the equipment to promote acid heating.

3. The system of claim 1, wherein the holder is used to position a rock sample plug for testing.

4. The system of claim 1, wherein acid that is introduced into the holder is formic, acetic, hydrochloric and/or gelled acid.

* * * * *